United States Patent
Hauer et al.

(10) Patent No.: US 8,153,408 B2
(45) Date of Patent: Apr. 10, 2012

(54) BIOCATALYTIC RACEMISATION OF ALPHA-HYDROXYKETONES

(75) Inventors: Bernhard Hauer, Fußgönheim (DE); Rainer Stürmer, Rödersheim-Gronau (DE); Bettina M. Nestl, Graz (AT); Wolfgang Kroutil, Graz (AT); Kurt Faber, Graz (AT)

(73) Assignee: BASF SE, Ludwigshafen (DE)

( * ) Notice: Subject to any disclaimer, the term of this patent is extended or adjusted under 35 U.S.C. 154(b) by 716 days.

(21) Appl. No.: 12/278,464

(22) PCT Filed: Jan. 31, 2007

(86) PCT No.: PCT/EP2007/050925
§ 371 (c)(1),
(2), (4) Date: Jan. 12, 2009

(87) PCT Pub. No.: WO2007/090767
PCT Pub. Date: Aug. 16, 2007

(65) Prior Publication Data
US 2009/0221046 A1    Sep. 3, 2009

(30) Foreign Application Priority Data

Feb. 9, 2006   (EP) .................................. 06101436

(51) Int. Cl.
*C12P 7/26* (2006.01)
(52) U.S. Cl. ....................................... 435/148; 435/183
(58) Field of Classification Search .................. 435/148, 435/183
See application file for complete search history.

(56) References Cited

OTHER PUBLICATIONS

Schnell, et al, "Enzymatic Racemisation and its Application to Synthetic Biotransformations," Advanced Synthesis and Catalysis, 2003, vol. 345, pp. 653-666.
Voloch, M et al, "Reduction of Acetoin to 2,3-Butanediol in Klebsiella pneumoniae: A New Model," Biotechnology and Bioengineering, 1983, vol. 25, No. 1, pp. 173-183.
Taylor, M.B., et al, "Stereoisomeric Specificities of 2,3-Butanediol Dehydrogenases," Biochimica et Biophysica Acta, 1960, vol. 39, pp. 448-457.

*Primary Examiner* — Chih-Min Kam
(74) *Attorney, Agent, or Firm* — Connolly Bove Lodge & Hutz LLP

(57) ABSTRACT

A process for the racemization of an optically active alpha-hydroxyketone by incubating said alpha-hydroxyketone in the presence of an acetoin racemase of *Lactobacillus*.

8 Claims, No Drawings

BIOCATALYTIC RACEMISATION OF ALPHA-HYDROXYKETONES

RELATED APPLICATIONS

This application is a national stage application (under 35 U.S.C. §371) of PCT/EP2007/050925, filed Jan. 31, 2007, which claims benefit of European Application No. 06101436.1, filed Feb. 9, 2006.

FIELD OF THE INVENTION

The invention relates to a process of biocatalytic racemisation of α-hydroxyketones (acyloins).

BACKGROUND OF THE INVENTION

Racemisation represents the key step in so-called deracemisation processes, which allow the quantitative transformation of a racemate into a single stereoisomeric product. Many chemical racemisation protocols require harsh reaction conditions and have therefore to be conducted ex-situ after separation of the material to be racemised from the chiral product (s) formed during kinetic resolution. Only few racemisation methods are consistent with mild reaction conditions and thus can be used in-situ, most notably transition metal catalysts.

The enzymatic interconversion of an acyloin (acetoin) has been ascribed to the action of a so-called acetoin racemase, whose existence was only postulated for the organism *Klebsiella* (M. Voloch, M. R. Ladisch, V. W. Rodwell, G. T. Tsao, Biotechnol. Bioeng. 1983, 25, 173-183.) but detailed data are not available.

OBJECT OF THE INVENTION

It was an object of the invention to provide a process which allows the complete trans-formation of racemic alpha-hydroxyketones into one optically active alpha-hydroxyketone or alpha-hydroxyketone-derivative.

DETAILED DESCRIPTION OF THE INVENTION

The present invention provides a process for the racemisation of an optically active alpha-hydroxyketone by incubating said alpha-hydroxyketone in the presence of an acetoin racemase of *Lactobacillus*.

The acetoin racemase has been classified in the Enzyme Classification System as E.C. 5.1.2.4 and is also named as acetylmethylcarbinol racemase.

Suitable organisms as a source for the acetoin racemase according to the invention are Lactobacilli. Preferred species of *Lactobacillus* are *L. paracasei, L. sakei, L. halotolerans, L. delbrueckii, L. confuses, L. oris*. These organisms are well known in the art and can be isolated by known procedures or can be received from public microorganism deposits.

*L. paracasei* can be received from DSM 20008, DSM 20207, DSM, 2649, ATCC 25598, NCIB 9713.

*L. sakei* can be received from DSM 20017, ATCC 15521.

*L. halotolerans* can be received from DSM 20190, ATCC 35410.

*L. delbrueckii* can be received from DSM 20074, ATCC 9649, NCIB 8130.

*L. confusus* can be received from DSM 20196, ATCC 10881, NCIB 9311.

*L. oris* can be received from DSM 4864, ATCC 49062, NCIB 8831.

Some of these Lactobacilli have been reclassified or their nomenclature has been updated. For example *Lactobacillus halotolerans* is also named Weissela halotolerans or *Lactobacillus confusus* is also named Weissela confusa. These synonyms are well known and are referenced e.g. in the DSMZ catalogue.

A preferred embodiment of the invention is a process for the racemisation of an optically active alpha-hydroxyketone by incubating said alpha-hydroxyketone in the presence of an acetoin racemase of *Lactobacillus*, where the alpha-hydroxyketone has the formula (1a) or (1b), $$R^1 \underset{R\ \overset{|}{OH}}{\overset{O}{\underset{\|}{C}}} R^2 \quad \underset{\text{racemase}}{\overset{\text{acetoin}}{\rightleftharpoons}} \quad R^1 \underset{S\ \overset{|}{OH}}{\overset{O}{\underset{\|}{C}}} R^2$$

(1a)            (1b)

wherein R1 and R2 are chosen independently from each other from optionally substituted alkyl groups, preferred C1-C10 alkyl groups, aryl groups, preferred homoaryl, such as phenyl, or naphtyl groups, which can be optionally substituted or heteroaryl groups such as pyridinyl or pyrimidinyl groups, or aralkyl groups, such as benzyl groups or cycloalkyl groups.

Preferred R1 and R2 residues are Methyl, Ethyl, n-Propyl, i-Propyl, n-Butyl, i-Butyl and tert. Butyl residues.

It is also possible that R1 is directly connected to R2 in such a way that a cyclic acetoin is formed. Preferably these cyclic acetoins are 5- to 8-membered rings. Preferred acetoins are (R)-2-Hydroxy-1,2,3,4-tetrahydronaphthalin-1-one or (R)-2-Hydroxyindan-1-one and the respective (S)-enantiomers.

In the above mentioned residues one or more H-atoms can be optionally substituted by groups such as OH, SH, CN, NO2, NH2, NH(alkyl), N(alkyl)2, F, Cl, Br, J, CO, COOH, COO(alkyl).

The incubation of the alpha-hydroxyketone with the acetoin racemase can be performed at a temperature between 0 and 80, preferably between 10 and 50° C.

The incubation is usually performed in aqueous phase, which can be adjusted to a specific pH value by adding buffer solutions. The optimum pH value is specific for the chosen enzyme and can be evaluated easily by routine experimentation. Usually a pH between 6 and 8 is chosen for the process according to the invention. It is possible to add organic solvents into the aqueous phase in order to improve the solubility of the substrates.

The acetoin racemase can be added by incubating the alpha-hydroxyketone with whole cells of the corresponding *Lactobacillus* strain. This is the preferred embodiment of the invention. It is also possible to isolate from the respective *Lactobacillus* strain the enzyme in a more or less purified form by applying routine steps of enzyme purification.

If the acetoin racemase is used in form of whole cells, the respective *Lactobacillus* strain is grown in a growth medium, preferably as described in the experimental section, and harvested. The whole cells can be used in the process according to the invention either immediately or stored, preferably in a lyophilized form, and used later.

Another aspect of the invention is a process for the production of an optically active acylated alpha-hydroxyketone by enantioselective acylation of an racemic alpha-hydroxyketone comprising a process for the racemisation of an optically active alpha-hydroxyketone by incubating said alpha-hydroxyketone in the presence of an acetoin racemase of *Lactobacillus*. Such a process is described in the following reaction scheme:

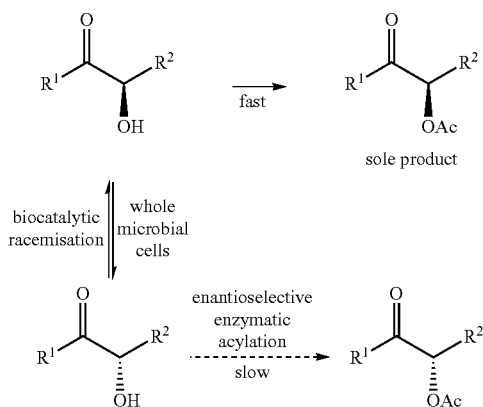

sole product

This process allows the complete transformation (100%) of the racemic substrate into an optically active acylated alpha-hydroxyketone.

Experimental Section

Whole microbial cells, in particular *Lactobacillus paracasei* subsp. *paracasei* DSM 20008, DSM 20207, DSM 2649, *Lactobacillus sakei* subsp. *sakei* DSM 20017, *Lactobacillus halotolerans* DSM 20190, *Lactobacillus delbrueckii* subsp. *delbrueckii* DSM 20074, *Lactobacillus confusus* DSM 20196 and *Lactobacillus oris* DSM 4864, were shown to racemise alpha-hydroxycarbonyl compounds 1-4 of the general structure shown below, where $R^1$ and $R^2$ are as follows:

| Substrate | $R^1$ | $R^2$ |
|---|---|---|
| (1) | —$CH_3$ | —$CH_3$ |
| (2) | —$C_6H_5$ | —$C_6H_5$ |
| (3) | —$CH_3$ | —$C_6H_5$ |
| (4) | —$C_6H_5$ | —$CH_3$ |

Preparation of Biocatalyst:

*Lactobacillus paracasei* subsp. *paracasei* DSM 20008, DSM 20207, DSM 2649, *Lactobacillus sakei* subsp. *sakei* DSM 20017, *Lactobacillus halotolerans* DSM 20190, *Lactobacillus delbrueckii* subsp. *delbrueckii* DSM 20074, *Lactobacillus confusus* DSM 20196 and *Lactobacillus oris* DSM 4864 were grown on medium #11 as suggested by DSMZ. The following components of the medium were sterilised in five separate groups: Group I: Casein peptone (10 g/L, Sigma), bacteriological peptone (10 g/L, Oxoid), yeast extract (5 g/L, Oxoid). Group II: Glucose (20 g/L, Fluka). Group III: Tween 80 (polyoxyethylene-sorbitan-monooleate, 1 g/L, Aldrich). Group IV: $K_2HPO_4$ (2 g/L, Merck). Group V: Na-acetate trihydrate (8.3 g/L, Fluka), $(NH_4)_2$-citrate (2 g/L, Fluka), $MgSO_4·7H_2O$ (0.2 g/L, Fluka), $MnSO_4·H_2O$ (0.05 g/L, Fluka).

Strains were grown in flask cultures without shaking at 30° C. (*Lactobacillus paracasei* subsp. *paracasei* DSM 20008, DSM 20207, DSM 2649, *Lactobacillus sakei* subsp. *sakei* DSM 20017, *Lactobacillus halotolerans* DSM 20190 and *Lactobacillus confusus* DSM 20196) and at 37° C. (*Lactobacillus delbrueckii* subsp. *delbrueckii* DSM 20074 and *Lactobacillus oris* DSM 4864). The microorganisms were grown for 3d. Then the cells were harvested by centrifugation (18000*g), washed twice with BIS-TRIS buffer (50 mM, $10^{-2}$ M $MgCl_2$, pH 6), lyophilised and stored at +4° C.

General procedure for the biocatalytic racemisation of α-hydroxycarbonyl compounds: *Lactobacillus* spp. were grown in medium #11 as suggested by DSMZ at 30° C. and 37° C., respectively, in flask cultures without shaking. After 3 days, the cells were harvested by centrifugation (18000*g), lyophilised and stored at +4° C. For the biocatalytic racemisation, 50 mg of whole lyophilised cells were rehydrated in 0.5 ml aqueous BIS-TRIS buffer (50 mM, $10^{-2}$ M $MgCl_2$, pH 6) for 1 h at 42° C. with shaking at 150 rpm. Substrates 1-4 (5 mg) were added followed by shaking of the reaction mixture with 150 rpm at 42° C. for 24 h, 48 h and 72 h. Then the reaction mixture was extracted with ethyl acetate and the organic phase was dried over sodium sulfate. The organic phase was evaporated under reduced pressure and the residue was dissolved in HPLC-eluent. The determination the enantiomeric excess of the substrate was carried out by HPLC on a chiral stationary phase. Analysis of the enantiomeric composition versus time gave the initial rates of racemisation, which are represented as % with respect to substrate (R)-1 sert as standard (100%).

Determination of Relative Rates of Racemisation for Substrates 1-4.

The biocatalytic racemisation of acyloins 1-4 was performed using rehydrated lyophilised (resting) cells of *Lactobacillus paracasei* subsp. *paracasei* DSM 20207 in aqueous buffer at pH 6, the racemisation of acyloins 5-6 by using rehydrated lyophilised (resting) cells of *Lactobacillus halotoleransi* DSM 20190. A fast racemisation rate was observed with acetoin (R)-(1), it's relative rate was arbitrarily set as standard (100%). High racemisation rates were also obtained for both enantiomers of substrate 2 and (R)-phenylacetylcarbinol (R)-(3). The relative racemisation rate of (R)-2-hydroxypropiophenone (4) was slightly reduced. (R)-2-Hydroxy-1,2,3,4-tetranaphtalin-1-one (R)-(5) and (R)-2-Hydroxyindane-1-one (R)-(6) show a high racemisation.

| Substrate | Relative Rate [%][a] | Racemization [%][b] |
|---|---|---|
| (R)-1 | 100 | 86 |
| (R)-2 | 56 | 78 |
| (S)-2 | 83 | 96 |
| (R)-3 | 67 | 50 |
| (R)-4 | 65 | 46 |
| (R)-5 | 77 | 92 |
| (R)-6 | 58 | 84 |

[a]Initial rate of racemisation relative to (R)-1 arbitrarily set as standard (100%);
[b]Extent of racemisation under standard conditions after 24 h.

The mechanism of the chemical racemisation of acyloins is generally regarded to proceed through the corresponding enediol intermediate. At neutral pH, racemisation of acyloins was reported to be a rather slow process (complete racemisation within 2 months), but is markedly enhanced at basic pH (e.g. pH 8.0-8.5) and in organic media it requires the presence of an organic base.

Groth Medium for the Biocatalystαα
DSM Medium 11:

| | |
|---|---|
| Casein peptone, tryptic digest | 10.00 g |
| Meat extract | 10.00 g |
| Yeast extract | 5.00 g |
| Glucose | 20.00 g |
| Tween 80 | 1.00 g |
| $K_2HPO_4$ | 2.00 g |
| Na-acetate | 5.00 g |
| $(NH_4)_2$ citrate | 2.00 g |
| $MgSO_4 \times 7 H_2O$ | 0.20 g |
| $MnSO4 \times H_2O$ | 0.05 g |
| Distilled water | 1000.00 ml |

Adjust pH to 6.2-6.5.

The invention claimed is:

1. A process for the racemisation of an optically active alpha-hydroxyketone comprising incubating said optically active alpha-hydroxyketone in the presence of an acetoin racemase of *Lactobacillus*, wherein said optically active alphahydroxyketone has the formula (1a) or (1b):

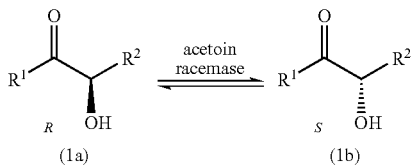

wherein $R^1$ and $R^2$ are, independently from each other, optionally substituted alkyl groups, optionally substituted aryl groups, optionally substituted aralkyl groups, or optionally substituted cycloalkyl groups.

2. The process of claim 1, wherein $R^1$ and $R^2$ are, independently from each other, methyl or phenyl.

3. The process of claim 1, wherein $R^1$ and $R^2$ are, independently from each other, 4-tert-butoxy or methyl.

4. The process of claim 1, where said optically active alpha-hydroxyketone of formula (1a) is (R)-2-Hydroxy-1,2,3,4-tetrahydronaphthalin-1-one or (R)-2-Hydroxyindan-1-one.

5. The process of claim 1, where said acetoin racemase of *Lactobacillus* is selected from the group consisting of *L. paracasei, L. sakei, L. halotolerans, L. delbrueckii, L. confusus,* and *L. oris*.

6. The process of claim 1, wherein said incubation is performed in the presence of whole cells of *Lactobacillus*.

7. The process of claim 1, wherein said incubation is performed at a temperature in the range of from 10° C. to 50° C.

8. A process for producing an optically active acylated alpha-hydroxyketone comprising (1) incubating an optically active alpha-hydroxyketone in the presence of an acetoin racemase of *Lactobacillus* and (2) enantioselectively acylating said racemic alpha-hydroxyketone, wherein said optically active alphahydroxyketone has the formula (1a) or (1b):

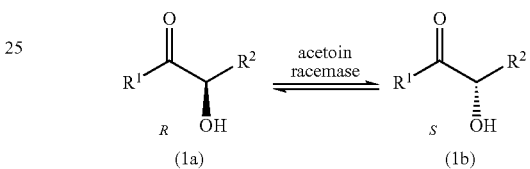

wherein $R^1$ and $R^2$ are, independently from each other, optionally substituted alkyl groups, optionally substituted aryl groups, optionally substituted aralkyl groups, or optionally substituted cycloalkyl groups.

* * * * *